United States Patent [19]

Lagow

[11] Patent Number: 5,716,708
[45] Date of Patent: Feb. 10, 1998

[54] ACETYLENIC CARBON ALLOTROPE

[76] Inventor: Richard J. Lagow, 6204 Shadow Mountain Dr., Austin, Tex. 78731

[21] Appl. No.: 375,115

[22] Filed: Jan. 19, 1995

Related U.S. Application Data

[63] Continuation-in-part of Ser. No. 374,476, Jan. 17, 1995, abandoned.

[51] Int. Cl.[6] ........................................ C08F 4/50
[52] U.S. Cl. ..................... 428/408; 423/445 R; 525/285; 526/328.1
[58] Field of Search ..................... 423/445 R; 525/202, 525/275, 285; 526/328.1; 428/408

[56] References Cited

U.S. PATENT DOCUMENTS

| | | | |
|---|---|---|---|
| 4,020,265 | 4/1977 | White | 526/285 |
| 4,273,906 | 6/1981 | Economy et al. | 526/285 |
| 4,362,680 | 12/1982 | Kobayashi et al. | 526/285 |
| 4,410,640 | 10/1983 | Kobayshi et al. | 526/285 |
| 4,496,702 | 1/1985 | Bolt et al. | 526/285 |
| 4,672,093 | 6/1987 | Wrek et al. | 525/328.1 |
| 5,304,583 | 4/1994 | Ogawa | 526/285 |

OTHER PUBLICATIONS

Cox, D.M., et al., "Carbon Clusters Revisted: The 'Special' Behavior of $C_{60}$ and Large Carbon Clusters", *J. Chem. Phys.*, vol. 88, No. 3, pp. 1588–1597 (1988).

Heinz Günter Viehe, "Darstellung und Reaktionen der Chloracetylenide in Flüssigem Ammoniak", *Chem. Ber.*, vol. 92, pp. 1270–1276, (1959).

Bierschenk, T.R., "Synthesis of Trifluorosilyl Organometallic Complexes from Trifluorosilyl Radicals and Metal Atoms", *J. Am. Chem. Soc.*, vol. 109, No. 16, pp. 4855–4860 (1987).

Sinclair, J.A., et al., "Synthesis of Unsymmetrical Conjugated Diynes via the Reaction of Lithium Dialkynydialkylborates with Iodine", *J. Org. Chem.*, vol. 41, No. 5, pp. 1078–1079 (1976).

McCullough, L.G., et al., "Why Terminal Alkynes Cannot be Metathesized. Preparation and Crystal Structure of a Deprotonated Tungstenacyclobutadiene Complex, $W(\eta^5-C_5H_5)[C_3(CMe_3)_2]Cl^{1a}$", *J. Am. Chem. Soc.*, vol. 105, pp. 6729–6730 (1983).

*Primary Examiner*—Archene Turner
*Attorney, Agent, or Firm*—Elizabeth A. Hanley; Mark D. Russett; Lahive & Cockfield, LLP

[57] ABSTRACT

A fourth allotrope of carbon, an acetylenic carbon allotrope, is described. The acetylenic carbon allotropes of the present invention are more soluble than the other known carbon allotropes in many common organic solvents and possesses other desirable characteristics, e.g. high electron density, ability to burn cleanly, and electrical conductive properties. Many uses for this fourth allotrope are described herein.

28 Claims, 13 Drawing Sheets

THE SYNTHESIS OF $(CH_3)_3C-C\equiv C-C\equiv C-C\equiv C-C\equiv C-C(CH_3)_3$.

OTHER PUBLICATIONS

Wagener, K. B., et al., "Acrylic Diene Metathesis (ADMET) Polymerization. Thermal, Ultraviolet, and Chemical Modification of ADMET Polyethers", *Macromolecules,* vol. 25, pp. 2049–2052 (1992).

Hay, A.S., "Oxidative Coupling of Acetylenes. II", *J. Org. Chem.,* vol. 27, pp. 3320–3321 (1962).

Lagow, R.J., et al., "New Methods for the Synthesis of Trifluoromethyl Organometallic Compounds", *Advances in Inorganic Chemistry and Radiochemistry,* vol. 23, pp. 177–210 (1979).

Curl, R.F., et al., "Fullerenes", *Scientific American,* pp. 54–63 (1991).

Little, W.A., "Possibility of Synthesizing an Organic Superconductor", *Physical Review,* vol. 134, No 6A, pp. A1416–A1424, (1964).

Rubin, Y. et al., "Solution–Spray Flash Vaccuum Pyrolysis: A New Method for the Synthesis of Linear Poliynes with Odd Numbers of C–C Bonds from Substituted 3,4–Dialkynyl–3–cyclobutene–1,2–diones", *J. Am. Chem. Soc.* vol., 113, pp. 6943–6949 (1991).

Diederich, F. et al., "All–Carbon Molecules: Evidence for the Generation of Cyclo[18] carbon from a Stable Organic Precursor", *Science,* vol. 245, pp. 1088–1090 (1989).

Eastmond, R., et al., "Silylation as a Protective Method for Terminal Alkynes in Oxidative Couplings", *Tetrahedron,* vol. 28, pp. 4601–4616 (1972).

Rohlfing, E.A., et al., "Production and Characterization of Supersonic Carbon Cluster Beams", *J. Chem. Phys.,* vol. 81, No. 7, pp. 3322–3330 (1984).

P.P.K. Smith, et al., "Carbyne Forms of Carbon: Do They Exist?", *Science,* vol. 216, pp. 984–986 (1982).

W. Krätschmer, et al., "Solid $C_{60}$: A New Form of Carbon", *Nature,* vol. 347, pp. 354–358 (1990).

Heath, J.R., et al., "The Formation of Long Carbon Chain Molecules During Laser Vaporizaton of Graphite", *J. Am. Chem. Soc.,* vol. 109, pp. 359–363, (1987).

1. PYREX REACTOR
2. TO VACUUM PUMP
3. GRAPHITE ROD
4. GRAPHITE BLOCK
5. 1.5 kW LASER
6. ZnSe WINDOW
7. O-RING
8. COOLING COIL
9. ARGON (OR HELIUM)
10. $C_2F_6$ (OR CYANOGEN, THE DASH LINE FOR CYANOGEN REACTION)
11. ELECTRODE (ONLY FOR $C_2F_6$ REACTION)
12. RADIO-FREQUENCY GENERATOR

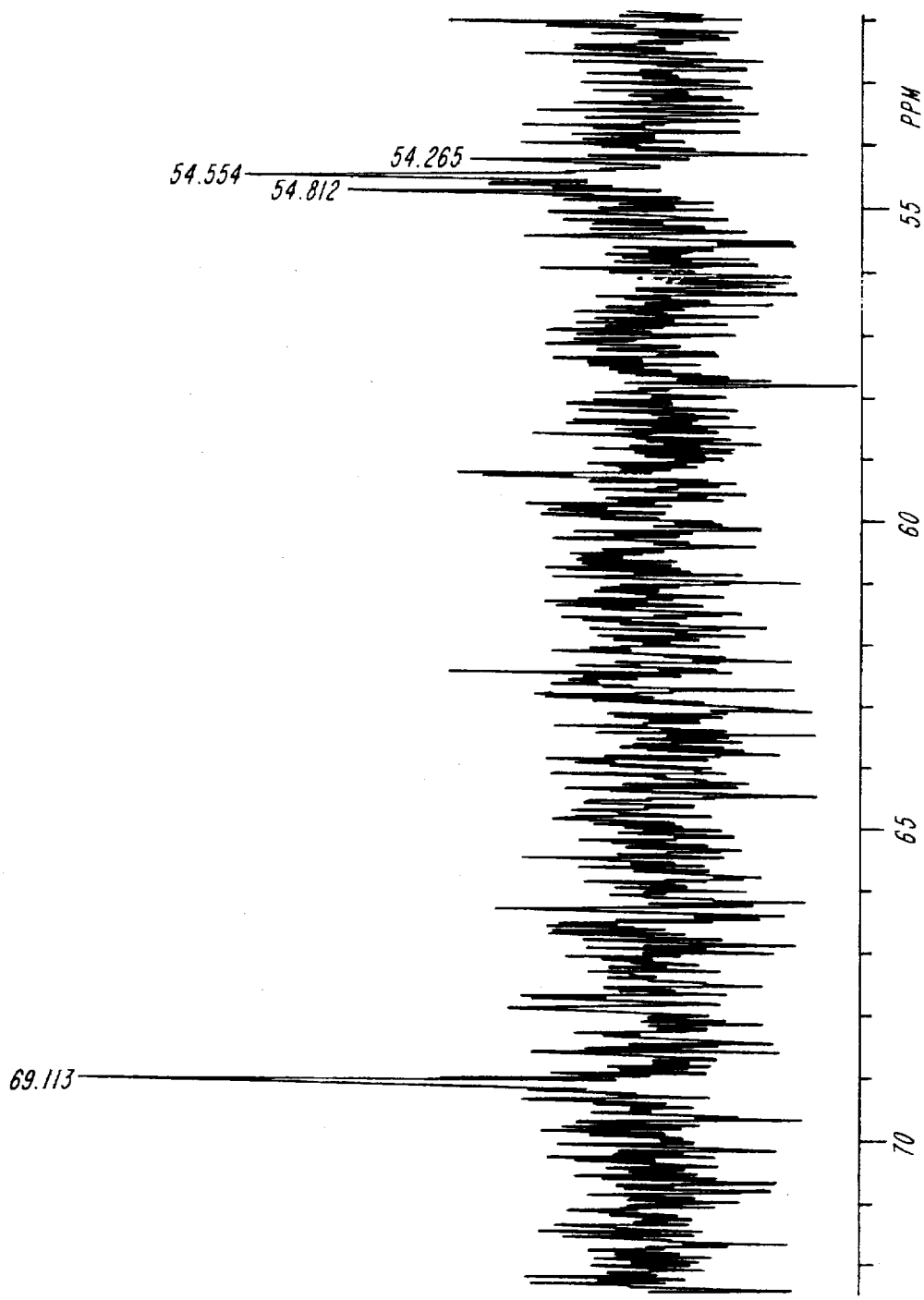

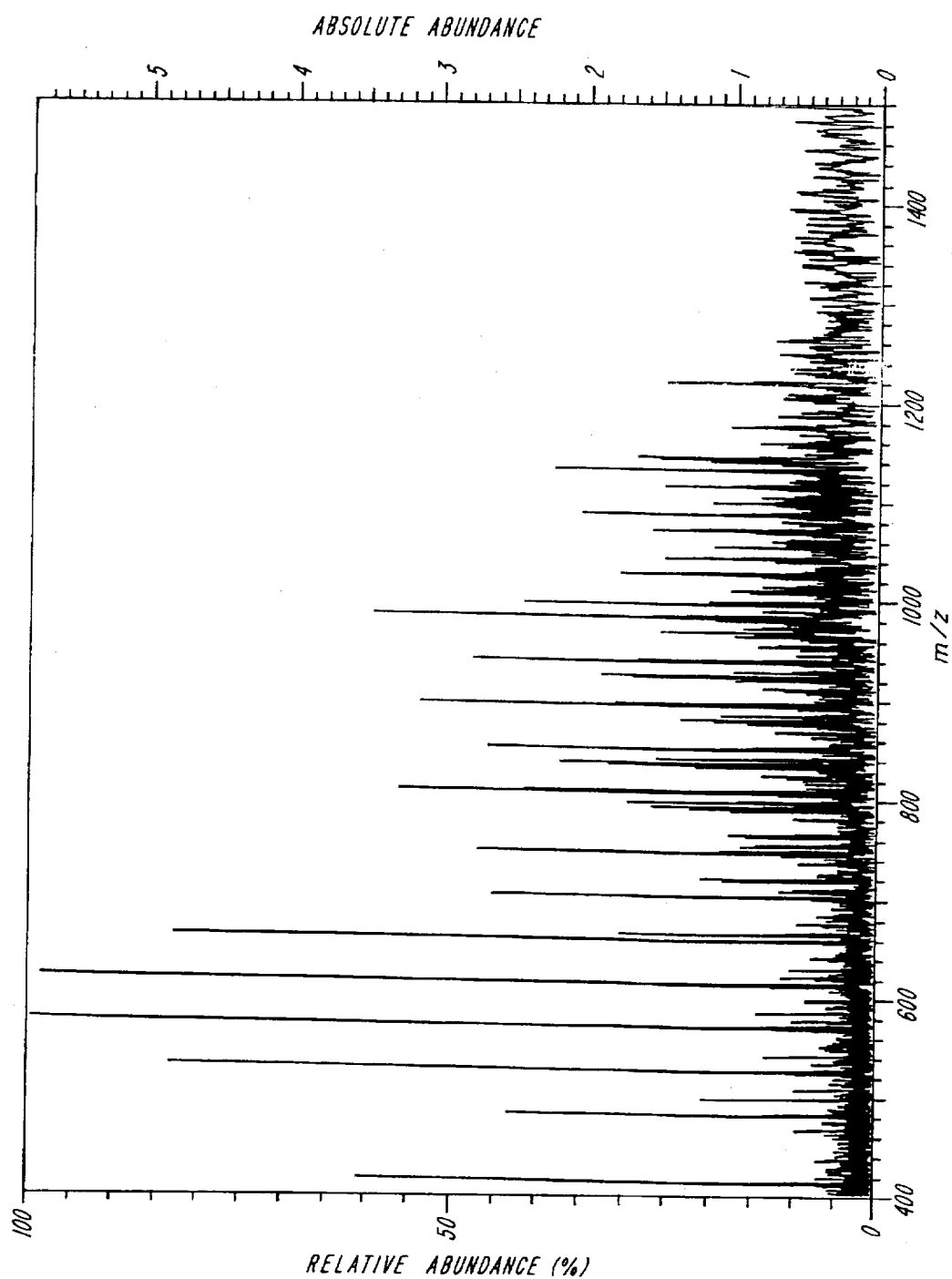

5,716,708

ACETYLENIC CARBON ALLOTROPE

RELATED APPLICATION

This application is a continuation-in-part application of U.S. Ser. No. 08/374,476, now abandoned, entitled LINEAR ACETYLENIC CARBON by Richard J. Lagow, filed on Jan. 17, 1995. The contents of the aforementioned parent application are expressly incorporated by reference.

GOVERNMENT SUPPORT

Work described herein has been supported by a grant from the Department of Energy (Grant DE-FG05-91ER12119). The U.S. Government may therefore have certain rights in the invention.

BACKGROUND OF THE INVENTION

Carbon is found in nature in several allotropic forms. Two well known allotropes of carbon are diamond and graphite. Diamond has a cubic structure formed by a tetrahedral lattice of sp3-bonded carbon atoms. This structure has great strength and makes diamond a hard material. Graphite is composed of sp2-hybridized carbon atoms bonded together in layers. Individual layers are stacked to form bulk graphite, which is quite soft; the layers are not strongly associated and so are able to slip relative to one another. This slipping of layers is generally believed to be the source of the lubricating qualities of graphite.

Other well-known forms of carbon include soot, charcoal, and other amorphous materials, which are all composed of finely divided graphite. Graphite is also known to exist as whiskers or fibers which have high tensile strength.

More recently, a third allotrope of carbon, the fullerenes, has been discovered and extensively studied (see e.g., "fullerenes" *Scient. Am.*, October, 1991, pp. 54–63). The fullerenes consist of sp2-hybridized carbons bonded into a closed shell. The simplest and most studied fullerene has 60 carbon atoms arranged in the form of a truncated icosahedron; the shape of this molecule resembles a soccer ball, and it has both 5- and 6-membered rings in its structure. Other fullerenes having 70, 84, and higher numbers of carbon atoms have also been characterized. A related structure is the carbon nanotube, which consists of carbon atoms arranged so as to form a cylinder.

The known allotropes of carbon are based either on sp3 (diamond) or sp2 (graphite, fullerenes, nanotubes) hybridization of carbon. The existence of other allotropes have been mentioned previously, however, the acetylenic carbon allotrope was generally held to be unstable. Although there were papers from the former Soviet Union in the 50s and 60s claiming that a new form of carbon called "carbyne" had been prepared (Mel'nichenko, V. M. et al., *Carbon* 21, 131 (1983), and references contained therein.), other workers have extensively studied their evidence and this contention is generally held to be incorrect (see e.g. P. P. K. Smith and P. R. Buseck, *Science* 216, 984 (1982); J. Jansta, F. P. Dousek, V. Patazelova, *Carbon* 13, 377 (1975); W. A. Little, *Phys. Rev.* 134, 1416 (1964); M. F. Hawthorne, Preliminary Reports, Memoranda and Technical Notes of the Materials Research Council Summer Conference, La Jolla, Calif., July, 1973 (NTIS)).

The synthesis of long-chain acetylenic carbon species [(α-ω-bis(triethylsilyl)polyynes up to 32 carbon atoms] with alternating single and triple bonds was reported by David Walton and co-workers in 1972 (R. Eastmond, T. R. Johnston, D. R. M. Walton, *Tetrahedron* 28, 4601 (1972).).

They prepared, using copper chloride (Hay coupling), mixtures of acetylenic carbon compounds that contained 2–16 acetylene units. Walton reported that beyond eight carbon atoms the chains became increasingly unstable with increasing length, and only the lowest members of the series were isolable.

Diederich and co-workers (F. Diederich et al., *Science* 245, 1088 (1989)) have reported the synthesis of mass spectrometric quantities of a $C_{18}$ alkyne-containing carbon ring by flash heating [18]annulene precursors. Diederich has also reported the synthesis of acetylenic carbon species containing up to 6 acetylene units (F. Diederich et al., *J. Am. Chem. Soc.* 113, 6943 (1991)).

SUMMARY OF THE INVENTION

The present invention is based, at least in part, on the discovery of a fourth allotrope of carbon being an acetylenic carbon allotrope. The acetylenic carbon allotropes of the present invention are more soluble than the other known carbon allotropes in many common organic solvents and possess other desirable characteristics, e.g. high electron density, ability to burn cleanly, and electrical conductive properties. Many uses for this fourth allotrope are described below.

The present invention pertains to a carbon compound. The carbon compound being substantially —C≡C— repeat units in a carbon chain which is endcapped and having a total number of carbon atoms which is greater than twelve not including the end capping groups. The carbon compound can have a formula as follows:

$$X_1-(C\equiv C)_n-X_2$$

wherein $X_1$ and $X_2$ are each independently capping end groups; and n is an integer greater than 16. The preferred acetylenic carbon allotropes of the present invention are long chained linear acetylenic carbon compounds.

BRIEF DESCRIPTION OF THE DRAWINGS

FIG. 8 is a $^{13}C$ NMR spectrum of —CN end capped acetylenic carbon chains in deuteroacetone.

FIG. 9A is the Fourier Transform high resolution mass spectrum (FTHRMS) of —CN endcapped acetylenic carbon chains.

DETAILED DESCRIPTION

Forms and Properties of the Acetylenic Carbon Allotropes

The present invention pertains to a carbon compound which is a fourth allotrope of carbon. The carbon compound being substantially —C≡C— repeat units in a carbon chain which is endcapped and having a total number of carbon atoms which is greater than twelve not including the endcapping groups. The carbon compound can have a formula as follows:

Figure 2:
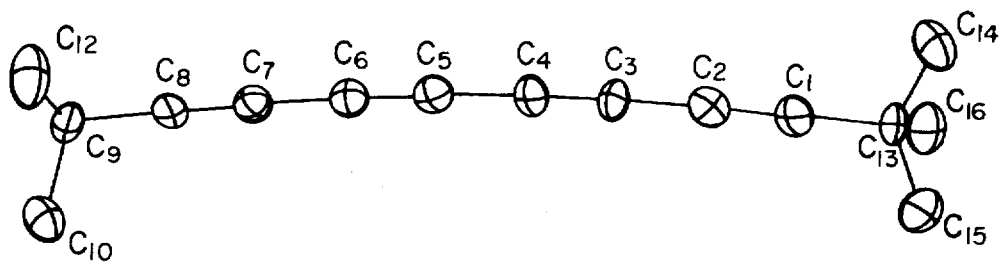
FIG. 2 is a table showing the bond distances and bond angles of $(CH_3)_3C$—C≡C—C≡C—C≡C—C≡C—C $(CH_3)_3$ as determined by X-ray crystallography.
Figure 3:
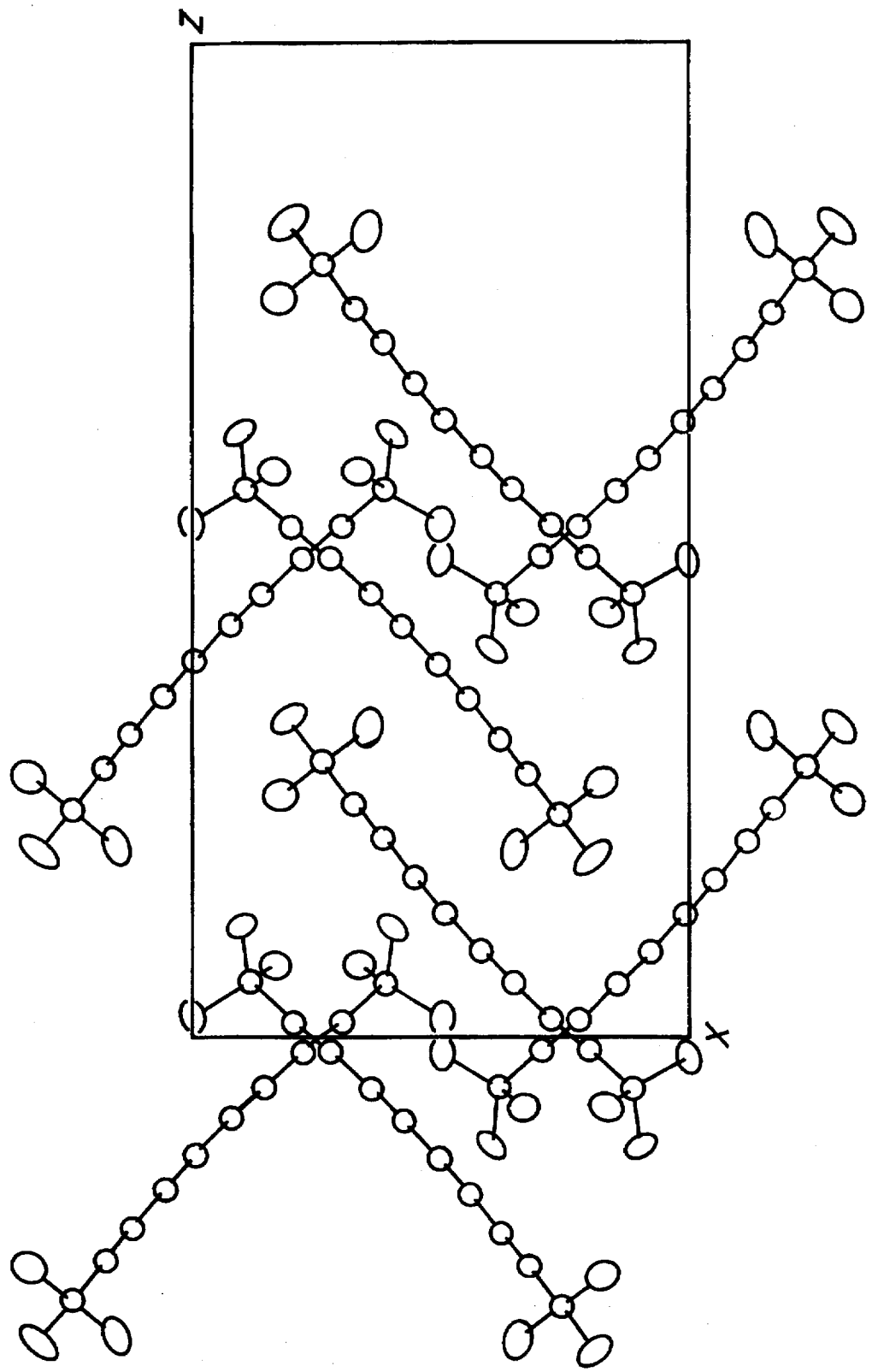
FIG. 3 depicts the unit cell packing of $(CH_3)_3C$—C≡C—C≡C—C≡C—C≡C—$C(CH_3)_3$ as determined by X-ray crystallography.

$X_1$ and $X_2$ are each independently capping end groups and n is an integer greater than 16. The acetylenic carbon allotrope contain acetylenic groups —(C≡C)— and further can be linear, branched or cyclic, i.e., the carbon chain can cyclize forming a ring. The language linear is intended to include slight curves such as that depicted in FIGS. 2 and 3. The preferred form of the carbon allotrope of the present invention is a linear acetylenic carbon allotrope. FIGS. 2 and 3 show the unit cell packing and bond angles and bond distances of a capped acetylenic compound. These Figures confirm that the carbon chains of the present allotropes have alternating single and triple bonds between the carbons and a slight curve.

The capping end groups are groups which are capable of attaching to the ends of the acetylenic carbon chains allowing for the formation of stable acetylenic carbon allotropes. The end groups typically are non-reactive, and block hydrogen transfer interchain (within the carbon chain). The end groups also typically are bulkier than hydrogen. The end groups can be organic or inorganic groups. Examples of end groups which can be used within the present invention include, but are not limited to, substituted and unsubstituted alkyl groups (e.g., tert-butyl, ethyl, propyl, methyl, and trifluoromethyl), nitrile, substituted and unsubstituted phenyl and triethylsilyl groups. The substituents on the end groups can be substituents which do not interfere with the end group's ability to perform its intended function, e.g., allowing for the formation of an acetylenic carbon allotrope.

The lengths of the carbon chain in the acetylenic carbon allotrope can vary depending on such factors as the desired end use of the allotrope and/or the desired total percent by weight of carbon in the allotrope, e.g. at least 97 percent carbon by weight. The length of the carbon chain between the two capping end groups can be greater than 32 carbon atoms. The length of the carbon chain also can be up to one million carbon atoms (synthesis can be conducted using organometallic polymerization techniques described below). Examples of "n" values that can be used in the above formula include: at least 25, at least 50, at least 100, at least 150, at least 200, or at least 250, at least 1000, 3000, 5000, 10000, 20000, 50000, etc. The "n" value can be any even integer between 1 and 500000 and the range can be any range contained within this range.

The present invention also pertains to a composition enriched in an acetylenic carbon allotrope. The acetylenic carbon allotrope contains greater than 12 carbon atoms bound to each other via alternating single and triple bonds in an isolated form. The term "enriched" is intended to include compositions wherein the acetylenic allotrope is the predominant component with or without significant amounts of other components. Other components or ingredients can be present with the carbon acetylenic allotrope, e.g. other carbon allotropes such as fullerene or traces of graphite. The acetylenic carbon allotropes in the enriched compositions can contain carbon atoms which are linearly arranged or which form a ring. The preferred acetylenic carbon allotropes are those long-chain linear allotropes described in detail above.

The present invention also pertains to endcapped acetylenic carbon allotropes. The endcapped acetylenic carbon allotropes contain greater than 32 carbon atoms arranged between two capping end groups forming the endcapped allotrope. The endcapped allotropes also can contain carbon atoms which are linearly arranged or which form a ring. The capping end groups are as described above.

The present invention even further pertains to an essentially fullerene-free acetylenic carbon allotrope. The language "essentially fullerene-free" is intended to include no detectable amounts of fullerene present in the acetylenic carbon allotrope. Detectable is intended to mean not detectable using a $^{13}$C NMR procedure. In the procedure the fullerene content in the sample of the allotrope is compared to a known sample containing fullerene.

The present invention even further pertains to a soluble carbon allotrope. The soluble carbon allotrope of the present invention is soluble in solvents which differ from toluene and molten metals but also toluene and molten metals. It is presently known that fullerene is sparsingly soluble in toluene and diamond and graphite are soluble in molten metals, e.g., molten iron and molten nickel. The acetylenic carbon allotropes of the present invention are the most soluble of the known carbon allotropes in common organic solvents.

The present invention even further pertains to a purified acetylenic carbon allotrope. The purified acetylenic carbon allotrope has greater than twelve carbon atoms. The language "purified acetylenic carbon allotrope" is intended to include allotropes which are free from any other material at least in amounts which are detectable. The term detectable is as defined above and it is intended to include detectable using a $^{13}$C NMR procedure.

The present invention even further pertains to a composition containing what would be considered significant amounts by weight of an acetylenic carbon allotrope. The compositions contain at least about 0.5 grams, at least about 1.0 grams, or at least about 2.0 grams. The synthesis methods described in here allow large scale production of the acetylenic carbon allotropes of the present invention.

The present invention further even further pertains to solutions of a carbon allotrope. The carbon allotrope is dissolved in the solution (no significant amount of undissolved carbon allotrope is detectable by the naked eye). The solvent can be selected from the group consisting of tetrahydrofuran, chloroform, deuterochloroform, acetonitrile, acetone, and deuteroacetone.

Another aspect of the invention pertains to carbon fibers made from the acetylenic carbon allotropes. Chains of the linearly arranged carbon atoms are combined or grow together to form an acetylenic carbon fiber. The chains can be intertwined with each other. The carbon fibers of the present invention have a tensile strength which is greater than that of a comparable graphite fiber, preferably at least two time greater than that of a comparable graphite fiber, and more preferably five times greater than that of a comparable graphite fiber. The fibers of the present invention are 100 times as strong as comparable nylon fibers. The tensile strength is measured using conventional techniques and the comparison between the two fibers is a side-by-side comparison. The fibers compared have to be comparable in that the fibers have to be the same size, e.g., the diameters being the same.

The acetylenic carbon allotropes of the present invention also can be altered or complexed. For example, the allotropes can be derivatized or coordination complexes can be formed using metals which coordinate with acetylenic groups.

Synthetic Methods for Producing the Carbon Allotropes of the Present Invention

The acetylenic carbon allotropes of the present invention can be prepared using several different synthetic methods. A synthetic method capable of preparing long-chain acetylenic carbon allotropes is similar to that previously used to prepare fullerenes. One of the synthetic methods of the present invention differs from a previously known synthetic method for fullerene by introducing end groups into the system which allows for the formation of the long-chain linear acetylenic carbon allotropes of the present invention, e.g., by suppressing fullerene production.

The present invention pertains to a method for preparing the endcapped acetylenic carbon allotropes. The method includes providing a carbon source and a source of end groups and polymerizing the carbon source in the presence of the source of end groups such that endcapped acetylenic carbon allotropes are formed. The carbon sources or targets and end group sources are described in detail below.

Many methods are known for the synthesis of simple alkynes. Illustrative but non-limiting examples include dehydrohalogenation of dihalides or vinyl halides, cleavage of allylic selenoxides or vinyl sulfides, elimination of vicinal quaternary ammonium hydroxides, and cleavage of enol phosphorinates.

Terminal alkynes can be coupled by a variety of techniques, including reaction with stoichiometric amounts of cupric salts in the presence of a base (the Eglinton reaction), use of catalytic cuprous salts in the presence of ammonia or ammonium chloride (the Glaser reaction) or TMEDA (the Hay coupling), or by the Cadiot-Chodkiewicz coupling of terminal alkynes with 1-bromoalkynes. Another methods of forming polyalkynes is reaction of lithium dialkyldialkynylborates with iodine to yield a symmetrical diyne (see, e.g., Sinclair and Brown, *J. Org. Chem.* 41, 1078 (1976)). Diederich et al. (*Science*, 245 1088 (1989) and references therein) utilized a retro-Diels-Alder reaction to construct a strained polyacetylene structure, and have also reported production of polyynes by the thermolysis of alkynylcyclobutene-1,2-diones (*J. Am. Chem. Soc.* 113, 6943 (1991)).

The formation of long acetylenic carbon compounds by repeated coupling of lithiobromoacetylene is detailed in Example 2, infra. This reaction is one example of a more general class of oligomerizations or polymerizations which are useful for synthesizing the acetylenic carbon compounds of the present invention. In general, the starting materials are of the form

where $X_1$ and $X_2$ are groups which may be eliminated according to the reaction

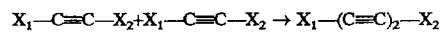

It is clear that the elimination process may occur repeatedly with extension of the acetylenic carbon chain. As shown in Example 2, suitable choices for $X_1$ and $X_2$ are Li and Br, which eliminate to form LiBr. Other suitable choices for $X_1$ and $X_2$ pairs are Si and F, Si and Cl, H and $OCH_3$, and the like. The choice of $X_1$ and $X_2$, and conditions suitable for the elimination, are well within the ability of one of skill in the art.

The formation of carbon clusters by vaporization of carbon targets has recently been reported (W. Krätschemer et al., *Nature* 347, 354 (1990) and references cited therein). The existence of a new allotrope of carbon known as buckminsterfullerene was first discovered with this technique. The formation of smaller clusters of carbon in the form of carbon chains was reported soon after the initial discovery of the fullerenes (Heath, J. R. et al., *J. Am. Chem. Soc.* 109, 359 (1987)). In that report, the carbon chains were not isolated, but were characterized solely on the basis of their mass spectrometric properties, so their structures are not well known. Carbon targets suitable for use in the present invention include allotropes such as graphite, diamond, fullerenes and nanotubes, as well as amorphous forms such as soot, carbon black, activated carbon, charcoal, lampblack and the like. The carbon target may be in the form of rods, sheets, fibers, whiskers, foams, powders, granules, pellets, flakes, foils, and the like. The carbon source may be vaporized by a variety of techniques including the use of lasers, plasma arcs, resistive or inductive heating, ion beams, electron beams, and the like. Third body gases useful in the present invention include any gas which does not react with the carbon species under the conditions of the experiment. Examples of suitable gases are helium, argon, krypton, xenon and other inert or noble gases. Use of heavier gases increases the chain length of the acetylenic carbon compounds formed as seen in Examples 4 and 5, infra. Therefore, use of xenon or other heavier noble gases will result in acetylenic chain lengths greater than 500 carbons.

It is well known that certain transition metals can form $\pi$-complexes with acetylene or acetylenic compounds. Examples of such metals are Nb, Mo, W, Fe, Ru, Co, Rh, Ir, Ni. Pd, Pt, and Cu. The $\pi$-complexes of acetylene with metals have been found to involve triple bond-to-metal interactions of one-to-one, two-to-one, one-to-two, two-to-two, and three-to-one (Patai, S. *The Chemistry of the Carbon-Carbon Triple Bond*, Parts 1 and 2, Ch. 1 and Ch. 4). Metathesis of alkynes has been studied extensively by Schrock (see e.g. McCullough et al. *J. Am. Chem. Soc.* 105, 6729 (1983) and references cited therein); it is possible to synthesize long-chain acetylenic carbon compounds with catalysts such as the Schrock catalyst or ADMET catalyst (Wagner, K. B. *Macromolecules* 25, 2049 (1992) and references cited therein) by using acetylenic starting materials and an olefinic capping group.

Uses for the Carbon Allotrope of the Present Invention

The acetylenic carbon compounds or allotropes of the present invention have many uses, some of which will be described below. The acetylenic allotropes will share many of the same uses as the extensively studied and used fullerene carbon allotrope. The acetylenic carbon allotropes can be used in conductive material and possess conductive properties in view of their electron density.

The acetylenic carbon allotropes also can be used for or in carbon coatings, e.g. graphite coatings. The carbon coatings can be used for many purposes, e.g., conductive or protective. The acetylenic carbon allotropes also can be used as precursors in both diamond (bulk and film) and graphite synthesis. The allotropes can be used as a fuel, e.g., a zero hydrogen fuel or a component of another type of fuel.

The acetylenic carbon allotropes of the present invention also can be used as a component or ingredient in many compositions, e.g., printing ink, lubricants (solid or liquid), toners, and films (thin films and high electron density). Another use for the allotropes of this invention in doped form, e.g. doped with an alkali metal or halogen, is in a superconductor material. The ordinarily skilled artisan would be able to envision many other uses for the allotropes or compounds of this invention based upon such factors as the known uses for the other known carbon allotropes and the properties possessed by the allotropes of this invention, e.g., solubility, thermal stability, and strength. There are many issued patents containing information pertinent to the above-described uses, at least some of which are as follows: U.S. Pat. Nos. 5,380,595 issued Jan. 10, 1995; 5,374,463 issued Dec. 20, 1994; 5,370,855 issued Dec. 6, 1994; 5,358,659 issued Oct. 25, 1994; 5,356,872 issued Oct. 18, 1994; 5,351,151 issued Sep. 27, 1994; 5,348,936 issued Sep. 20, 1994; 5,341,639 issued Aug. 30, 1994; 5,310,669 issued May 10, 1994; 5,302,474 issued Apr. 12, 1994; 5,296,536 issued Mar. 22, 1994; 5,292,444 issued Mar. 8, 1994; and 5,232,810 issued Aug. 3, 1993. The ordinarily skilled artisan would know how to substitute or add the allotrope of the present invention for or to that described in the aforementioned issued patents.

The following invention is further illustrated by the following examples, which should not be construed as further limiting. The contents of all references, pending patent applications and published patents, cited throughout this application are hereby expressly incorporated by reference.

EXAMPLE 1

Synthesis of a t-butyl Capped Acetylenic Model Compound

Figure 1:
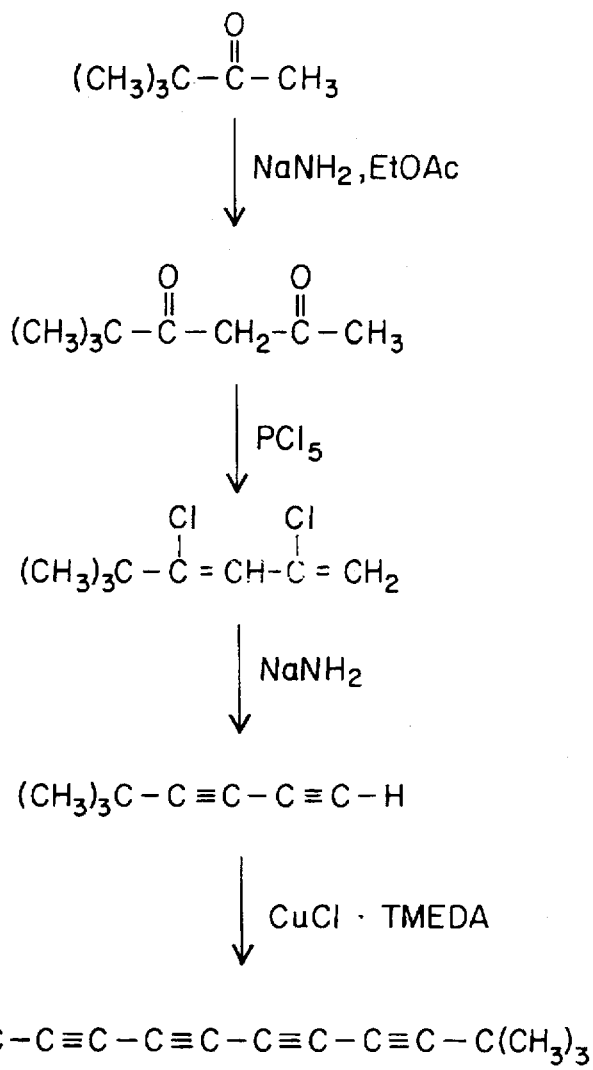
FIG. 1 depicts the scheme used for the synthesis of $(CH_3)_3C$—C≡C—C≡C—C≡C—C≡C—$C(CH_3)_3$.

An eight-carbon acetylenic chain endcapped with t-butyl groups was synthesized by the following procedure, summarized in FIG. 1:

Methyl t-butyl ketone was condensed with ethyl acetate in the presence of sodamide to yield 5,5-dimethyl-2,4-hexanedione. This material was reacted with phosphorus pentachloride to yield the divinyl chloride, which was in turn dehydrohalogenated with sodamide to give 5,5-dimethyl-1,3-hexadiyne. This alkyne was then dimerized using the procedure of Hay (see e.g. Hay, A. S., *J. Org. Chem.* 27, 3320 (1962)), using copper(I) chloride-tetramethylethylenediamine (TMEDA) complex as the catalyst, to yield the desired t-butyl endcapped tetrayne. The tetrayne melted at 99° C. and decomposed between 130° C. and 140° C. It is also stable to moderate pressures; exposure to 40 kbar pressure for one hour caused no changes in the IR spectrum, and at 60 kbar only about 2% graphitization was seen.

Figure 4C:
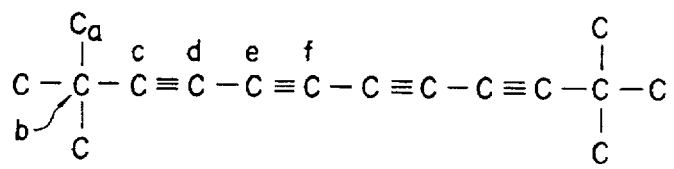
FIG. 4 shows the $^{13}C$ NMR spectrum of $(CH_3)_3C$—C≡C—C≡C—C≡C—C≡C—$C(CH_3)_3$.
Figure 4B:
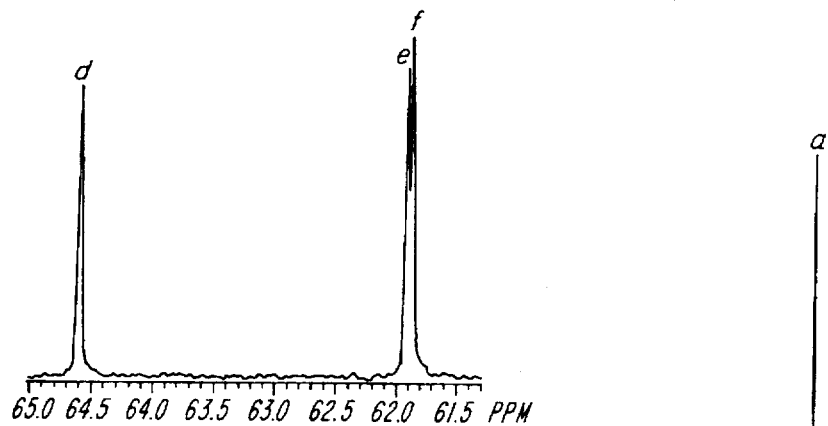
Figure 4A:
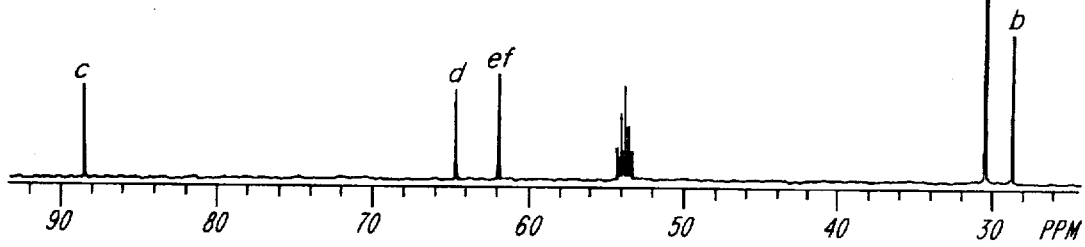

The crystal structure of this compound is shown in FIGS. 2 and 3. It is interesting that the acetylenic bond angles are not exactly 180° (FIGS. 2 and 3). The $^{13}C$ NMR spectrum of this material is shown in FIG. 4; all the resonances are identified except the solvent peak at around 54 ppm.

EXAMPLE 2

Synthesis of Phenyl Capped Acetylenic Carbon Products

Phenyl endcapped acetylenic chains were made by a modification of the conditions of Viehe (H. G. Viehe, *Chem. Ber.* 92, 1270 (1959)). The original reference describes the reaction of lithiobromoacetylene in liquid ammonia. The improved procedure given below was found to give better results.

Figure 5:
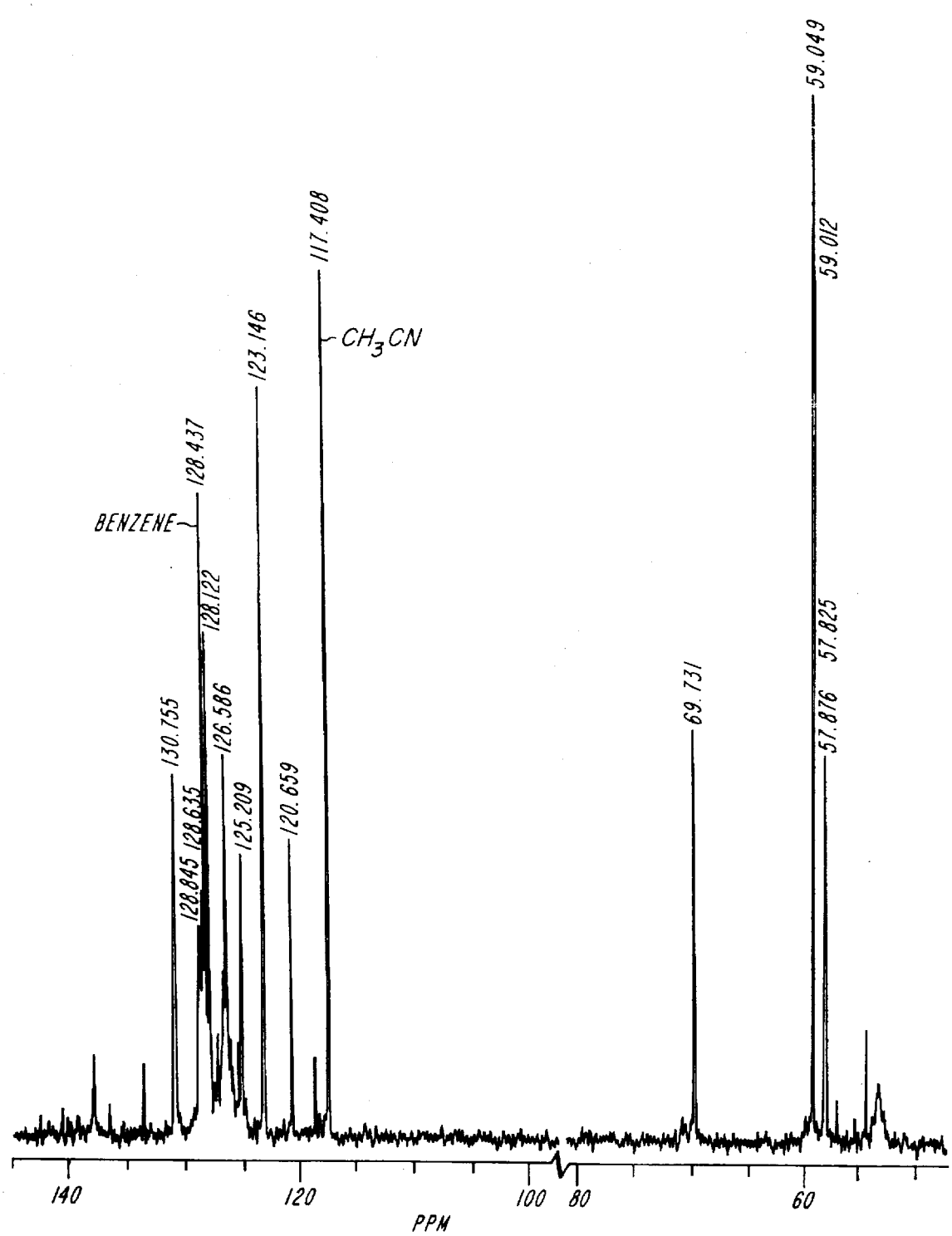
FIG. 5 shows the $^{13}C$ NMR spectrum of products of the condensation of Li—C≡C—Br.
Figure 6A:
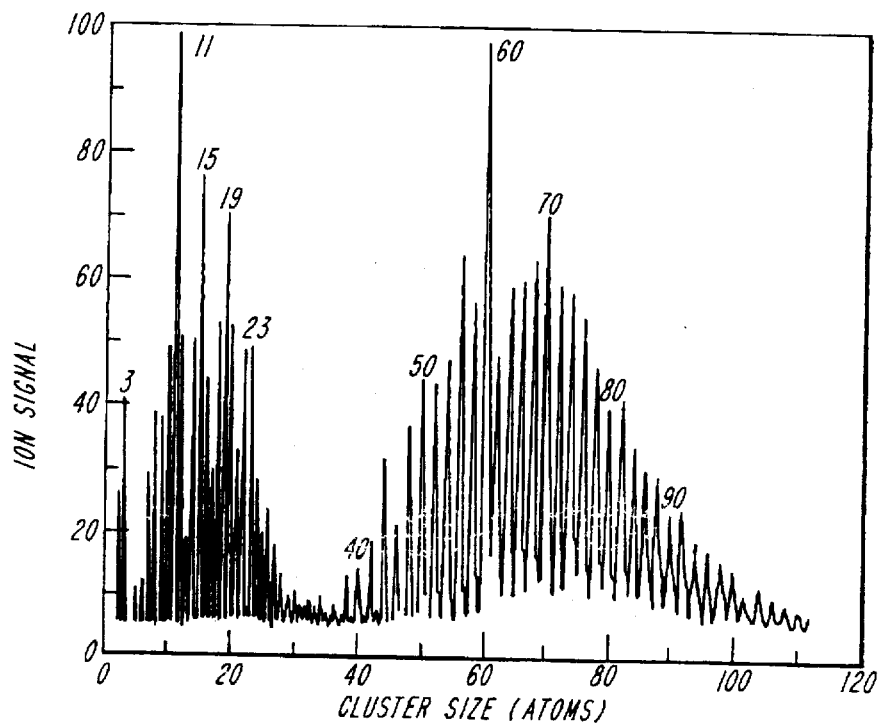
FIG. 6A shows the low molecular weight region of the mass spectrum of carbon cluster beams by Kaldor and coworkers (from E. A. Rohlfing, D. M. Cox, A. Kaldor, *J. Chem. Phys.* 81, 3322 (1984)).
Figure 6B:
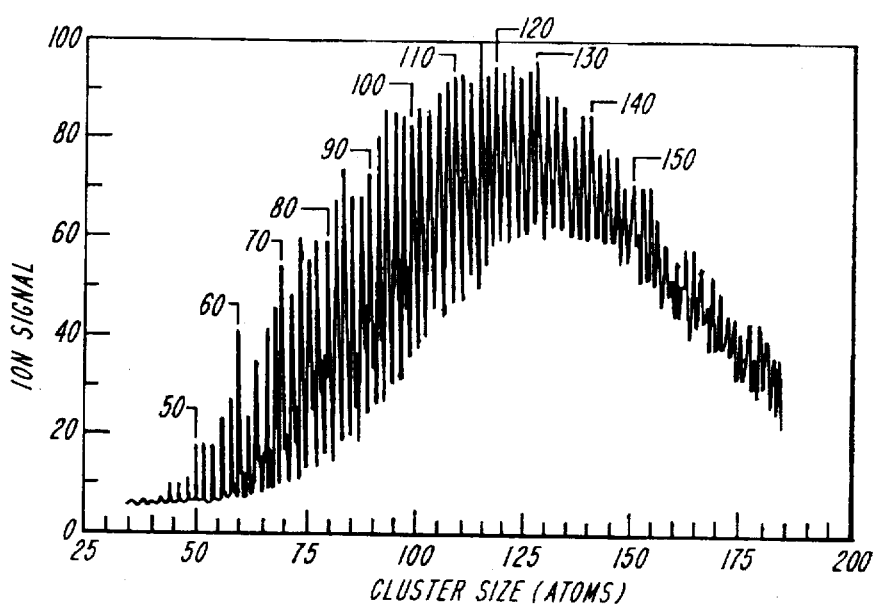
FIG. 6B shows the high molecular weight region of the mass spectrum of carbon cluster beams by Kaldor and coworkers as in FIG. 6A.

A 500 ml, 3-neck round-bottom flask was charged with 130 ml dry acetonitrile and cooled to −40°C with an acetonitrile/liquid nitrogen slush. 10.8 ml of 1.8M phenyllithium in hexanes was added under an inert atmosphere; then 0.538 ml (65 mmol) of 1,2-dibromoethylene was added to the yellow solution. After three hours the solution color had changed from yellow to burnt orange. The solution was allowed to stir overnight. Phenyl bromide (0.35 ml) was then added and allowed to stir overnight. The reaction mixture was filtered and the solvent and volatile components removed under reduced pressure. The resulting reddish oil was then analyzed. The mixture of products could not be separated on conventional alumina coitus due to the reactivity of the products toward alumina. The reaction mixture was analyzed by mass spectrometry, and the results were consistent with the formation of acetylenic chains having 16, 24, and 28 carbon atoms, the chains being capped at both ends by phenyl groups. The $^{13}C$ NMR of the product mixture is shown in FIG. 5. Mass spectrometry indicated that a 24-carbon cyclic acetylenic compound was also present.

EXAMPLE 3

Synthesis of a Long Chain Nitrile Capped Acetylenic Carbon Allotrope

The apparatus shown in FIG. 7 was used for the gas-phase synthesis of the acetylenic carbon allotrope with nitrile endcaps as described below. In this example, the electrodes 11 and radio-frequency generator 12 were not used. This apparatus was designed to have dimensions, mean free paths, and partial gas pressures similar to those obtained with the apparatus of Krätschmer and Huffman (W. Krätschmer, L. D. Lamb, K. Fostiropoulos, D. R. Huffman, *Nature* 347, 354 (1990)).

Graphite was vaporized using a Spectra-Physics 820 1.5 kilowatt, C. W., $CO_2$ laser into the apparatus shown in FIG. 7 with a 90% helium/10% cyanogen mixture at 0.2 atm of pressure. Multigram quantities of graphite could be vaporized for more than one hour. The reaction apparatus was at room temperature. The walls of the reactor were washed down with toluene after the run was finished; typically 0.5 to 1 gram quantities of products were obtained in a one hour run. The toluene extract was then analyzed for fullerenes and other species by $^{13}C$ NMR. Fullerenes were not normally present, although occasionally a very minor amount of $C_{60}$ and $C_{70}$ was observed. A sample of the toluene extract was evaporated to dryness and then redissolved in tetrahydrofuran (THF) to concentrate the acetylenic compounds and remove any fullerenes formed. The THF was then removed under vacuum and the extracted linear carbon capped species were dissolved in $CDCl_3$ for $^{13}C$ NMR analysis. A typical $^{13}C$ NMR spectrum is shown in FIG. 8. The spectrum clearly shows acetylenic carbon compounds with peaks at 54.265, 54.554, 54.812 and 69.113 ppm. A mass spectral analysis of the length of the acetylenic chains produced in the experiment was performed with a stainless steel probe coated with a solid residue of the THF extract. Mass spectra were taken with a Nd:YAG laser desorption using a Fourier Transform Ion Cyclotron Resonance Mass Spectrometer with a dual cell ion trapping assembly controlled by a Nicolet 1280 Data Station including a 3.0-T superconducting magnet. A typical spectrum observed around mass number 1200 (100 carbon atoms) shown in FIGS. 7A and 7B exhibits a repetitive carbon (24 mass unit) pattern. It is difficult to distinguish the nitrile capping groups on the end of a long chain from a chain of identical length containing all carbon atoms.

EXAMPLE 4

Synthesis of a Long Chain Trifluoromethyl Capped Acetylenic Carbon Allotrope

Figure 10:
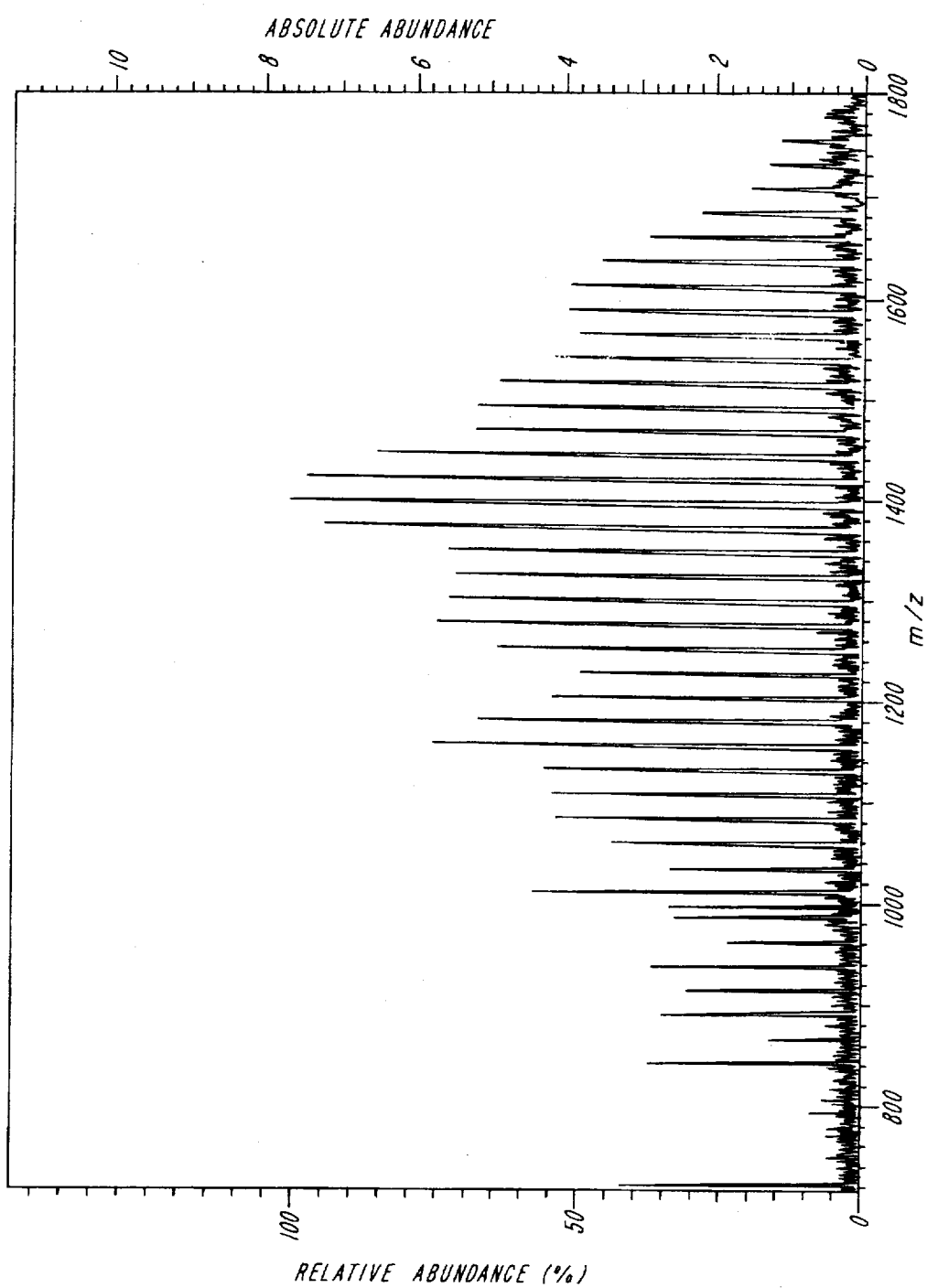
FIG. 10 is the FTHRMS of $\text{CF}_3$ end capped acetylenic carbon chains produced with helium as a third body gas.
Figure 11:
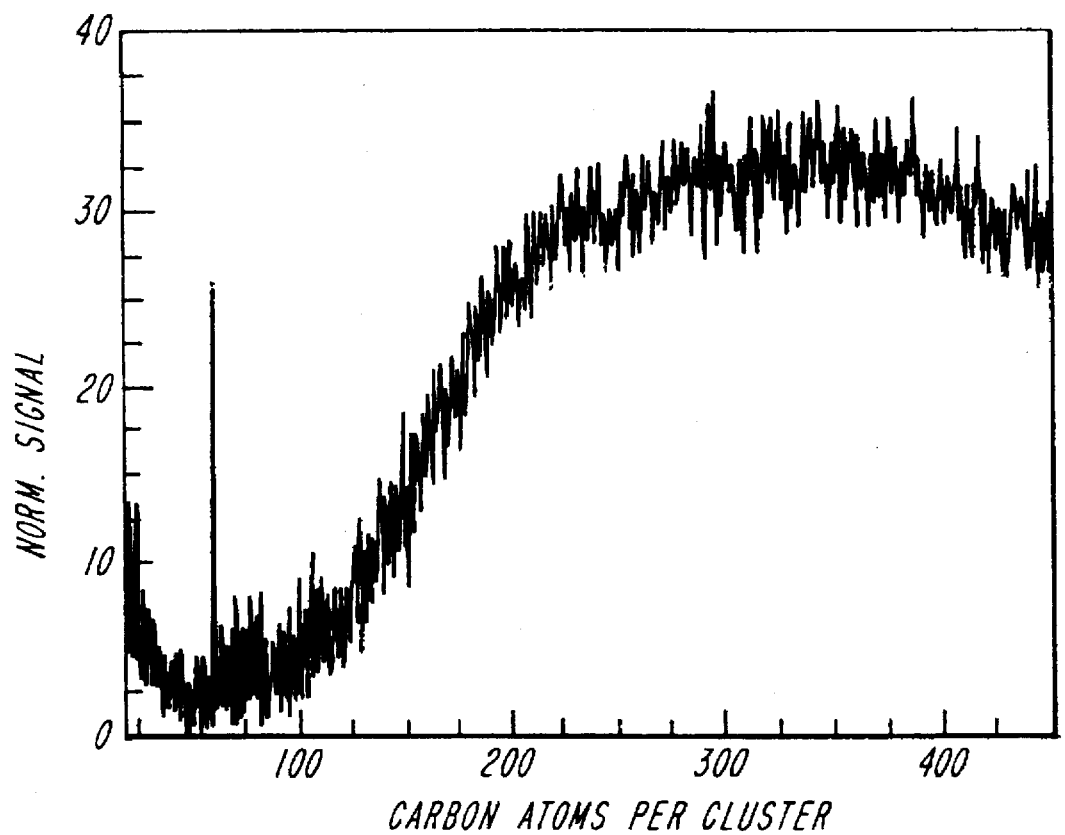
FIG. 11 is the mass spectrum of carbon clusters produced by Kaldor and coworkers using argon as the third body gas (from A. Kaldor, D. M. Cox, K. C. Reichmann, *J. Chem. Phys.* 88, 1588 (1988)).

Trifluoromethyl-capped acetylenic carbon chains were obtained by a modification of the above procedure. In this example, the tubing indicated in phantom in FIG. 7 is not used. Trifluoromethyl radicals were produced by the action a radiofrequency discharge on hexafluoroethane, and the trifluoromethyl radicals were cooled and "sandwiched," as described in Example 5, infra. The third body gas was helium. The mass spectrum of trifluoromethyl-capped acetylenic chains is shown in FIG. 10. The carbon clusters can be distinctly seen. The materials prepared and extracted in the $CF_3$ capping experiments, like the compounds prepared in the nitrile capping experiments of Example 3, were amber to dark brown in color both in solution and in the solid (powdered) state.

EXAMPLE 5

Figure 7:
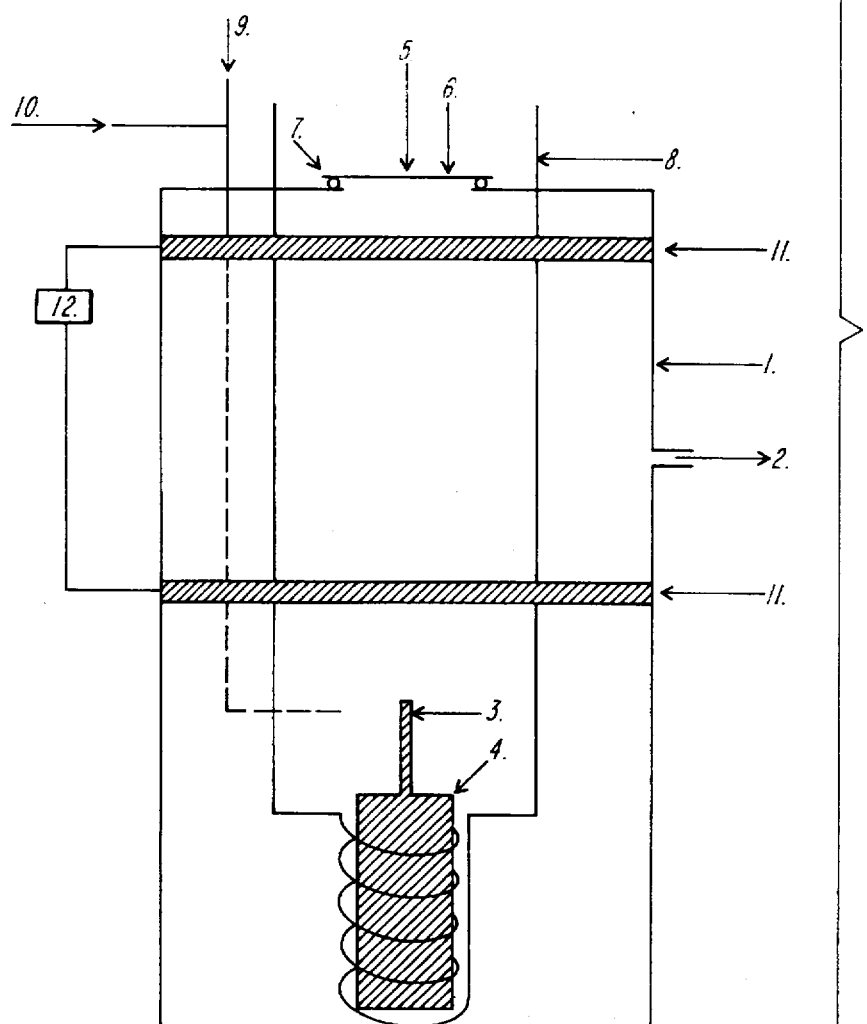
FIG. 7 shows the apparatus used to produce acetylenic carbon chains by vaporization of graphite.
Figure 9B:
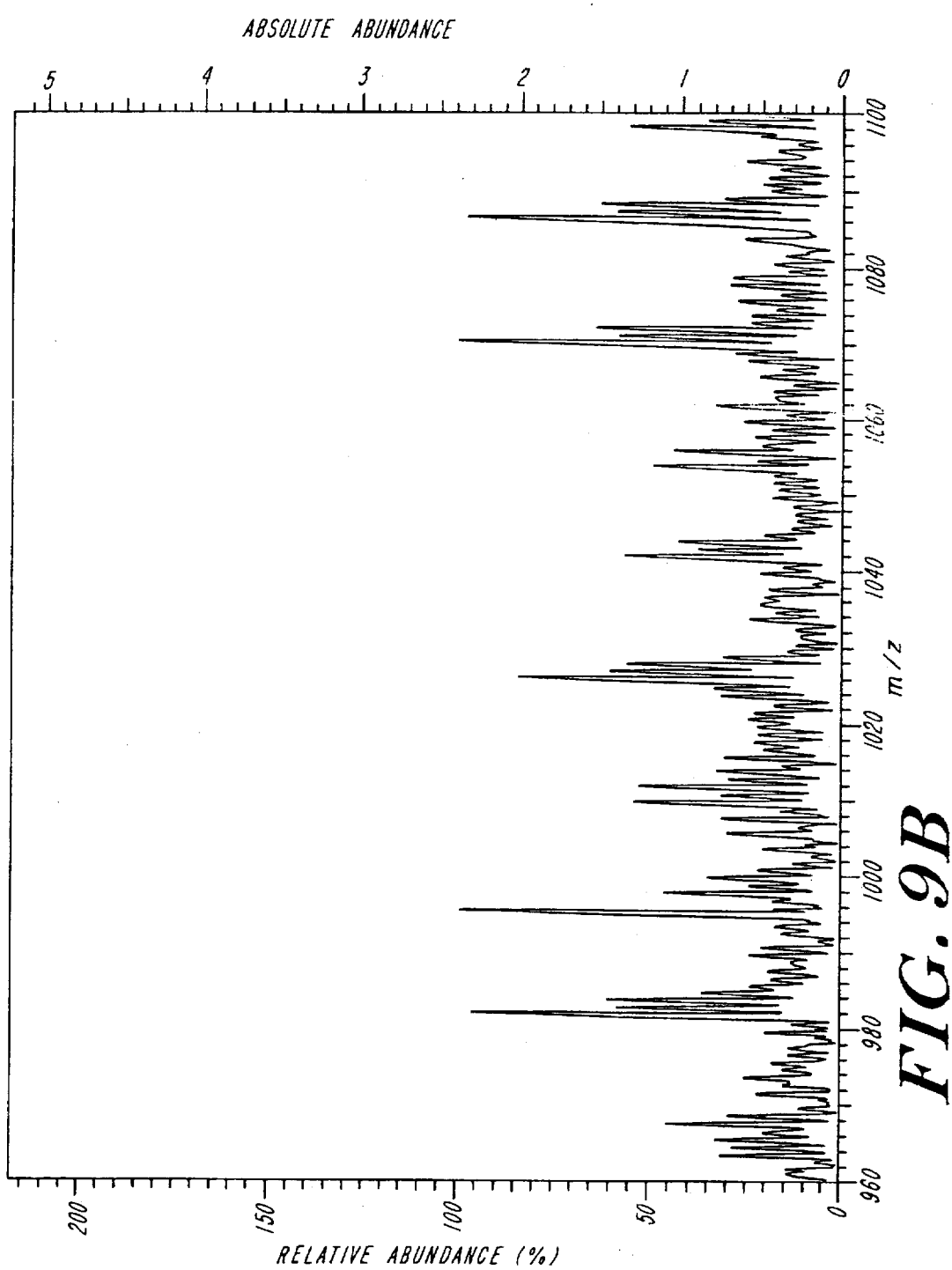
FIG. 9B is a detail, from 960 to 1100 mass units, of the spectrum shown in FIG. 9A.

Synthesis of a Long Chain Trifluoromethyl Capped Acetylenic Carbon Allotrope Using Helium as the Third Body Gas Long trifluoromethyl-capped acetylenic chains were made by the following procedure:

The apparatus shown in FIG. 7 was used as described in previous examples. The third body gas was argon at a pressure of about 0.2 atm. The trifluoromethyl radicals were generated by passing hexafluoroethane through a 10 Mhz radiofrequency discharge, as previously described (J. A. Morrison and R. J. Lagow, *Advances in Inorganic and Radiochemistry* 23, 177 (1979); T. R. Bierschenk et al., *J. Am. Chem. Soc.* 109, 4855 (1987)) with about 20 watts of power applied. To obtain the benefit of both gas phase and surface end capping reactions, the walls of the glass reactor were cooled to $-196°$ C., and trifluoromethyl radicals were condensed on the walls. The carbon was then vaporized as before, but the laser was periodically turned off and more trifluoromethyl radicals allowed to condense on the wall. This procedure resulted in "sandwiching" of the trifluoromethyl radicals between layers of cryogenically cooled carbon. This low-temperature approach may have the effect of stabilizing carbon chains terminated with delocalized electron end caps. Reaction between trifluoromethyl radicals and carbon chains may occur as the mixture is warmed, in addition to capping reactions which occur in the gas phase.

Figure 12:
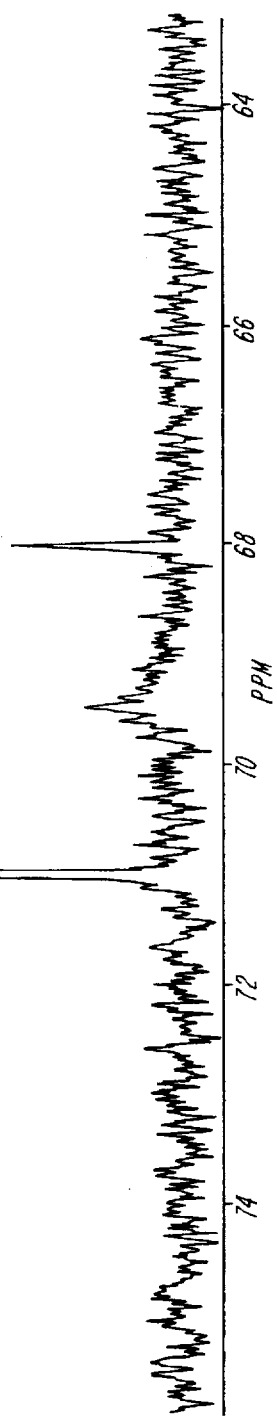
FIG. 12 is a $^{13}$C NMR spectrum in deuteroacetone of $\text{CF}_3$ end capped acetylenic carbon chains produced with argon as a third body gas.

As described in Example 3, supra, the acetylenic carbon products were purified by dissolving in toluene followed by evaporation of the solvent and redissolving in THF. The products obtained are amber to dark-brown in color. On many runs there was no detectable fullerene production, while on other runs small amount of fullerene were seen in the toluene fraction. The THF extracted sample was then dissolved in deuteroacetone and the $^{13}C$ NMR was obtained, as shown in FIG. 12. The largest peak is centered at 71.0282 ppm. No other carbon-containing species were observed from 10 to 200 ppm in the $^{13}C$ NMR spectrum.

Figure 13:
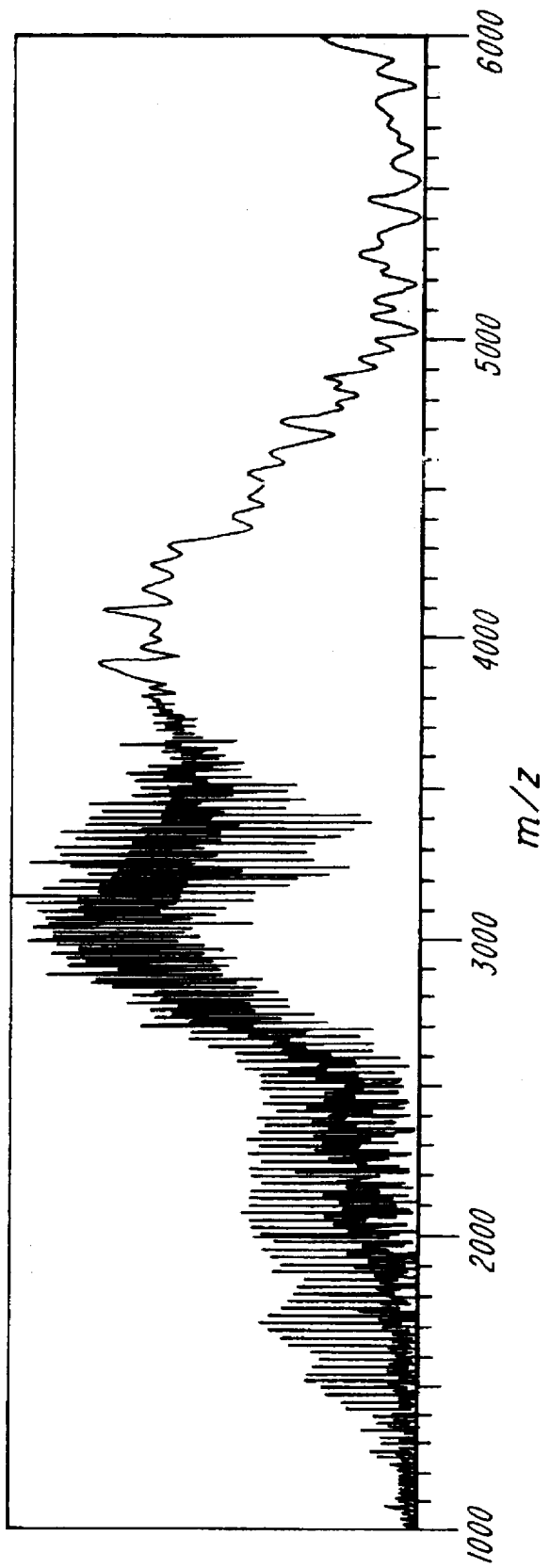
FIG. 13 is a Fourier transform mass spectrum of $\text{CF}_3$ end capped acetylenic carbon chains produced with argon as a third body gas.

A Fourier-transform infrared (IR) spectrum was run on the sample in deuteroacetone, and the solvent spectrum was then subtracted. A very strong band at $1200$ cm$^{-1}$, obscuring some of the C≡C bending modes of the linear carbon chain, provided definitive evidence of trifluoromethyl substitution. A $^{19}F$ NMR spectrum in $CDCl_3$ showed a strong sharp signal for trifluoromethyl groups at $-54.7$ ppm from $CFCl_3$. The mass spectrum was obtained as described in Example 3. A large envelope with an average molecular weight of 3600 (300 carbon atom chain) was observed (shown in FIG. 13), with peaks 24 mass numbers apart.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

I claim:

1. A stable carbon compound, comprising:
    substantially —C≡C— repeat units in a carbon chain which is endcapped and having a total number of carbon atoms which is greater than thirty-two not including the end capping groups.

2. The carbon compound of claim 1 which has a formula as follows:

wherein $X_1$ and $X_2$ are each independently capping end groups; and
    n is an integer greater than 16.

3. The carbon compound of claim 2 wherein n is an integer from 25 to 50.

4. The carbon compound of claim 2 wherein n is an integer from 51 to 100.

5. The carbon compound of claim 2 wherein n is an integer from 101 to 200.

6. The carbon compound of claim 2 wherein n is an integer from 201 to 400.

7. The carbon compound of claim 2 wherein n is an integer from 401 to 1000.

8. The carbon compound of claim 2 wherein n is an integer from 1001 to 5000.

9. The carbon compound of claim 2 wherein n is an integer between 5001 and 10000.

10. The carbon compound of claim 2 wherein the capping end groups are non-reactive.

11. The carbon compound of claim 2 wherein the capping end groups block interchain hydrogen transfer.

12. The carbon compound of claim 2 wherein n is an integer between 10,001 to 100,000.

13. The carbon compound of claim 2 wherein the capping end groups are each independently selected from the group consisting of tert-butyl, methyl, trifluoromethyl, nitrile, phenyl and triethylsilyl.

14. An enriched composition, comprising:
    an acetylenic carbon allotrope having greater than thirty-two carbon atoms bound to each other via alternating single and triple bonds in an enriched form.

15. The enriched composition of claim 14 wherein the carbon atoms in the allotrope are linearly arranged.

16. The enriched composition of claim 14 wherein the carbon atoms in the allotrope form a ring.

17. A stable endcapped acetylenic carbon allotrope, comprising:
    greater than thirty two carbon atoms arranged between two capping end groups forming a stable endcapped acetylenic carbon allotrope.

18. An endcapped acetylenic carbon allotrope of claim 17 wherein the carbon atoms are linearly arranged.

19. An essentially fullerene-free acetylenic carbon allotrope, comprising:

greater than thirty-two carbon atoms bound to each other via alternating single and triple bonds forming an acetylenic carbon allotrope, said allotrope being essentially free of fullerene.

20. A soluble carbon allotrope, comprising:

greater than thirty-two linearly arranged carbon atoms forming a soluble carbon allotrope which is soluble in solvents which differ from toluene and molten metals.

21. An acetylenic carbon allotrope, comprising:

greater than thirty-two linearly arranged carbon atoms having a thermal stability such that the allotrope does not crosslink at temperatures below 130° C.

22. A purified acetylenic carbon allotrope, comprising:

greater than thirty-two linearly arranged carbon atoms forming a pure acetylenic carbon allotrope.

23. A stable endcapped acetylenic carbon allotrope, comprising:

greater than thirty-two carbon atoms linearly arranged between two end groups forming a stable endcapped acetylenic carbon allotrope, provided that at least one of the end groups is not a triethyl silyl protecting group.

24. A composition of an acetylenic carbon allotrope, comprising:

an acetylenic carbon allotrope in an amount of at least 0.5 grams.

25. The composition of claim 24 wherein the amount is at least 1.0 grams.

26. The composition of claim 25 wherein the amount is at least 2.0 grams.

27. A solution of an carbon allotrope, comprising:

a carbon allotrope dissolved in a solvent, provided that the solvent is not toluene or a molten metal.

28. A solution of an carbon allotrope, comprising:

a carbon allotrope dissolved in a solvent, wherein the solvent is selected from the group consisting of tetrahydrofuran, chloroform, deuterochloroform, acetonitrile, acetone, and deuteroacetone.

\* \* \* \* \*